(12) United States Patent  
Bond et al.

(10) Patent No.: US 9,308,340 B2  
(45) Date of Patent: Apr. 12, 2016

(54) ENDOTRACHEAL TUBE HOLDER

(75) Inventors: Brian Bond, Woburn, MA (US); Chinawut P. Paesang, Cumberland, RI (US); Tara Larkin, Millville, MA (US); Fang Yin Dong, Shanghai (CN); Joshua N. Brezack, Warwick, RI (US)

(73) Assignee: Dale Medical Products, Inc., Plainville, MA (US)

( * ) Notice: Subject to any disclaimer, the term of this patent is extended or adjusted under 35 U.S.C. 154(b) by 25 days.

(21) Appl. No.: 13/291,455

(22) Filed: Nov. 8, 2011

(65) Prior Publication Data

US 2012/0168571 A1 Jul. 5, 2012

Related U.S. Application Data

(60) Provisional application No. 61/410,979, filed on Nov. 8, 2010.

(51) Int. Cl.  
*F16L 3/08* (2006.01)  
*A61M 16/04* (2006.01)  
*A61M 25/02* (2006.01)

(52) U.S. Cl.  
CPC .......... *A61M 16/0488* (2013.01); *A61M 25/02* (2013.01); *A61M 2025/022* (2013.01); *A61M 2025/0206* (2013.01)

(58) Field of Classification Search  
USPC .............. 248/70, 73, 74.1, 74.2, 74.4, 75, 49; 128/207.17, 207.14, 207.11, 217.15, 128/217.16, 861, 200.24, 200.26, 848  
See application file for complete search history.

(56) References Cited

U.S. PATENT DOCUMENTS

| | | | | |
|---|---|---|---|---|
| 3,602,227 A | * | 8/1971 | Andrew | 128/207.17 |
| 3,774,616 A | * | 11/1973 | White et al. | 128/200.26 |
| 3,946,742 A | * | 3/1976 | Eross | 128/207.17 |
| 3,993,081 A | * | 11/1976 | Cussell | 128/207.14 |
| 4,141,524 A | | 2/1979 | Corvese, Jr. | |

(Continued)

FOREIGN PATENT DOCUMENTS

WO WO 2010/033109 A1 3/2010

OTHER PUBLICATIONS

Ambu® Endotracheal Tube Holders, from CardinalHealth, downloaded from the internet: http://www.cardinal.com/us/en/distributedproducts/ASP/320264040.asp?cat=med_surg on Jul. 30, 2014.

(Continued)

*Primary Examiner* — Monica Millner  
(74) *Attorney, Agent, or Firm* — Finnegan, Henderson, Farabow, Garrett & Dunner LLP.

(57) ABSTRACT

An endotracheal tube holder is provided. The tube holder allows adjustment of the position of an endotracheal tube during use. In some embodiments the tube holder comprises a body portion, wherein the body portion is elongated and comprises an elongated opening. The tube holder also comprises a tube grasping mechanism and an attachment mechanism for adjustably securing the tube grasping mechanism to the body portion. The attachment mechanism comprises a rod member configured to pass through the elongated opening, a widened proximal body connected to a proximal end of the rod member; and a widened distal body attached to a distal end of the rod member, having a size that prevents the widened distal body from passing through the elongated opening to secure the attachment mechanism to the body portion.

24 Claims, 11 Drawing Sheets

(56) References Cited

U.S. PATENT DOCUMENTS

| | | | |
|---|---|---|---|
| 4,191,180 A | | 3/1980 | Colley et al. |
| 4,223,671 A | | 9/1980 | Muto |
| 4,249,529 A | * | 2/1981 | Nestor et al. ............. 128/207.17 |
| 4,351,331 A | * | 9/1982 | Gereg ...................... 128/207.17 |
| 4,449,527 A | * | 5/1984 | Hinton ..................... 128/207.17 |
| 4,832,019 A | * | 5/1989 | Weinstein et al. ........ 128/207.17 |
| 4,906,234 A | * | 3/1990 | Voychehovski ................. 604/79 |
| 5,069,206 A | * | 12/1991 | Crosbie ..................... 128/207.17 |
| 5,345,931 A | | 9/1994 | Battaglia, Jr. |
| 5,398,679 A | * | 3/1995 | Freed ........................ 128/207.17 |
| 5,419,319 A | * | 5/1995 | Werner ..................... 128/207.17 |
| 5,437,273 A | * | 8/1995 | Bates et al. .............. 128/207.17 |
| 5,490,504 A | | 2/1996 | Vrona et al. |
| 5,507,460 A | * | 4/1996 | Schneider ................ 248/225.21 |
| 5,671,732 A | * | 9/1997 | Bowen ...................... 128/207.17 |
| 5,782,236 A | * | 7/1998 | Ess ........................... 128/207.17 |
| 5,806,516 A | * | 9/1998 | Beattie ..................... 128/207.17 |
| 5,829,430 A | * | 11/1998 | Islava ....................... 128/200.26 |
| 5,934,276 A | * | 8/1999 | Fabro et al. ............. 128/207.17 |
| 6,029,668 A | * | 2/2000 | Freed ........................ 128/207.17 |
| 6,105,577 A | * | 8/2000 | Varner ..................... 128/207.17 |
| 6,408,850 B1 | * | 6/2002 | Sudge ....................... 128/207.17 |
| 6,578,576 B1 | | 6/2003 | Taormina et al. ........ 128/207.17 |
| 7,000,609 B2 | * | 2/2006 | Kleen ....................... 128/202.27 |
| 7,063,088 B1 | | 6/2006 | Christopher ............. 128/207.17 |
| 7,124,755 B2 | * | 10/2006 | Van Hooser ................. 128/845 |
| 7,231,921 B2 | * | 6/2007 | Palmer ..................... 128/207.17 |
| 8,256,427 B2 | * | 9/2012 | Chang et al. .................. 128/861 |
| 8,360,063 B2 | * | 1/2013 | Liland ...................... 128/207.11 |
| 2003/0154987 A1 | * | 8/2003 | Palmer ..................... 128/207.14 |
| 2004/0094161 A1 | * | 5/2004 | Palmer ..................... 128/207.17 |
| 2004/0232286 A1 | * | 11/2004 | Newkirk et al. ............. 248/68.1 |
| 2005/0092328 A1 | * | 5/2005 | Herrick et al. ........... 128/207.17 |
| 2005/0133038 A1 | * | 6/2005 | Rutter ....................... 128/207.17 |
| 2006/0081256 A1 | * | 4/2006 | Palmer ..................... 128/207.17 |
| 2008/0202529 A1 | * | 8/2008 | Flory et al. ............... 128/207.17 |
| 2009/0211572 A1 | * | 8/2009 | Matera ..................... 128/200.26 |
| 2009/0229616 A1 | * | 9/2009 | Liland ...................... 128/207.14 |
| 2011/0210215 A1 | * | 9/2011 | Nitsche et al. ............... 248/74.1 |
| 2011/0220127 A1 | * | 9/2011 | Chang et al. .................. 128/861 |
| 2012/0037756 A1 | * | 2/2012 | Guthke et al. ................ 244/131 |
| 2013/0061853 A1 | * | 3/2013 | De Iulio et al. .......... 128/207.14 |
| 2013/0174844 A1 | * | 7/2013 | Doll et al. ................ 128/204.18 |
| 2013/0233321 A1 | * | 9/2013 | Singh ....................... 128/207.15 |

OTHER PUBLICATIONS

Adjustable ET Tube Holder Latex-Free, from Marpac Inc., downloaded from the internet: http://www.marpacinc.com/etadjustable.htm on Jul. 30, 2014.

International Search Report and Written Opinion for PCT/US2011/059769 mailed Feb. 10, 2012, from the International Search Authority of the European Patent Office.

* cited by examiner

ENDOTRACHEAL TUBE HOLDER

PRIORITY

This application claims priority under 35 U.S.C. §119 to U.S. Provisional Patent Application No. 61/410,979, which was filed on Nov. 8, 2010, and is herein incorporated by reference.

FIELD

The present disclosure relates to tube holders, and more specifically, to endotracheal tube holders.

Endotracheal tubes are used in a variety of settings including in critical care, intensive care units, or under general anesthesia. However, most endotracheal tube holders only allow an endotracheal tube to be held in a single, fixed position, which can create problems, especially during long term use. The present disclosure provides endotracheal tube holders that allow easy adjustment of the position of an endotracheal tube either before or during use.

SUMMARY

One embodiment consistent with the present disclosure includes an endotracheal tube holder. The endotracheal tube holder comprises a body portion, wherein the body portion is elongated and comprises an elongated opening. The endotracheal tube holder also comprises a tube grasping mechanism, and an attachment mechanism for adjustably securing the tube grasping mechanism to the body portion. The attachment mechanism comprises a rod member configured to pass through the elongated opening, a widened proximal body connected to a proximal end of the rod member, and a widened distal body attached to a distal end of the rod member, having a size that prevents the widened distal body from passing through the elongated opening to secure the attachment mechanism to the body portion.

In certain embodiments of the present disclosure, the elongated opening includes a wide opening for receiving the widened distal body. In certain embodiments, the widened distal body has a spring like property along at least one dimension configured to being forcibly pushed through the wide opening and for locking behind the body portion. Moreover, in certain embodiments, the widened distal body has a spring like property along at least one dimension configured to being forcibly pushed through a section of the elongated opening and for locking behind the body portion.

In certain embodiments of the present disclosure, the rod member comprises a threaded rod. In certain embodiments, at least one of the widened proximal body and the widened distal body includes a threaded locking cap such that rotation of the locking cap with respect to the threaded rod changes a distance between the widened proximal body and the widened distal body to clamp or release the attachment mechanism to or from the body portion.

In certain embodiments of the present disclosure, the tube grasping mechanism comprises a widened end surface in which a middle opening is formed for receiving the rod member, wherein the rod member is rigidly connected to the widened distal body at the distal end, and wherein the widened proximal body includes the locking cap, such that the threaded rod passes through the elongated opening and the middle opening and is threadably connected to the locking cap.

In certain embodiments of the present disclosure, the tube grasping mechanism comprises a widened end surface in which a middle opening is formed for receiving the rod member, wherein the widened end surface is for attaching to the body portion, and wherein the widened proximal body and the widened distal body sandwich between them the body portion and the widened end surface. In certain embodiments, the body portion is curved for conforming to the shape of the face of a patient.

In certain embodiments, the tube grasping mechanism comprises an upper semicircular region and a lower semicircular region pivotably attached to the upper semicircular region. In certain embodiments, the upper semicircular region and the lower semicircular region comprise teeth to lock the lower semicircular region to the upper semicircular region and secure a tube therebetween. In certain embodiments, the lower semicircular region includes a tail end and the upper semicircular region includes a pincer configured to receive and lock the tail end and accordingly secure a tube between the upper and the lower semicircular regions. In certain embodiments, the tail end is toothed on at least one surface.

In certain embodiments, the body portion further comprises widened pad regions at opposite ends for lying against the face of a patient. In certain embodiments, the tube holder further comprises a band opening on each of the widened pad regions for receiving a flexible band for tying around the head or the neck of the patient.

In certain embodiments, the tube holder further comprises an arm that connects the tube grasping mechanism to the attachment mechanism. In certain embodiments, the elongated opening includes a toothed surface on at least one side.

Another embodiment consistent with the present disclosure includes an endotracheal tube holder which comprises a body portion, wherein the body portion is elongated and comprises an elongated opening, and a tube grasping mechanism rigidly connected to an attachment mechanism for adjustably securing the tube grasping mechanism to the body portion. In certain embodiments, the attachment mechanism comprises a rod member that passes through the elongated opening, and widened surfaces attached to the opposite sides of the rod member, which install on opposite sides of the elongated opening form a clamping mechanism for securing the tube grasping mechanism to the body portion.

In certain embodiments, the rod member comprises a threaded body that is connected at least one end to a threaded locking cap such that rotation of the locking cap with respect to the rod member changes a distance between the widened surfaces on opposite sides of the elongated opening to clamp or release the attachment mechanism.

BRIEF DESCRIPTION OF THE DRAWINGS

The accompanying drawings, which are incorporated in and constitute a part of this specification, illustrate exemplary embodiments consistent with the principles of the present invention.

DETAILED DESCRIPTION

Figure 1:
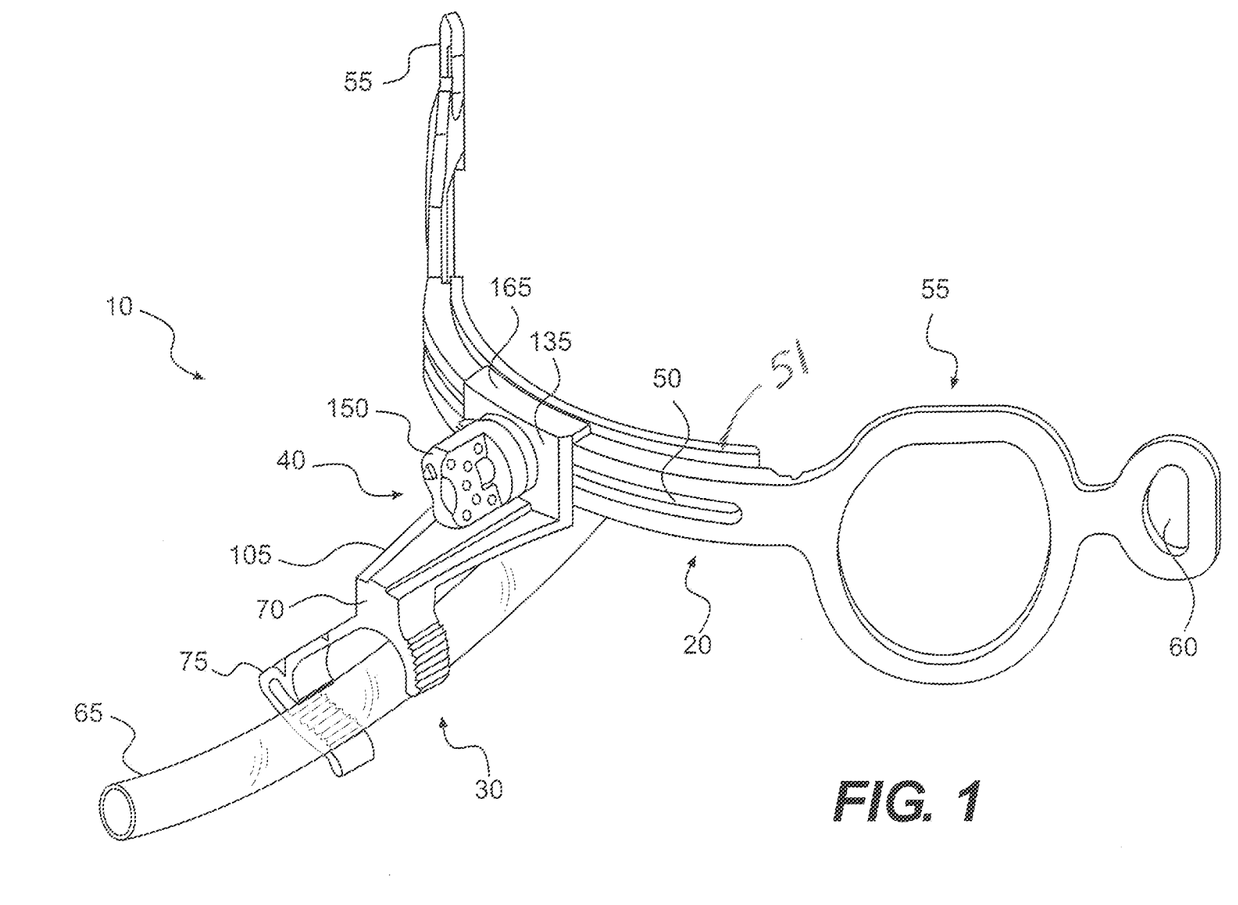
FIG. 1 provides a prospective view of an endotracheal tube holder, according to certain embodiments of present disclosure.

The present disclosure provides endotracheal tube holders that will allow adjustment of the position of an endotracheal tube either before or during use. FIG. 1 provides a perspective view of an endotracheal tube holder 10, according to certain embodiments. As shown, the endotracheal tube holder 10 includes an elongated body portion 20, a tube grasping mechanism 30, and an attachment mechanism 40 for adjustably securing the tube grasping mechanism 30 to the body portion 20.

As shown in FIG. 1, the elongated, body portion 20 can include an elongated opening 50 that extends along the length of the curved body portion. The elongated opening 50 can be configured to engage with the attachment mechanism 40 to secure the tube grasping mechanism 30 to the elongated, body portion 20. The body portion 20 can be formed from a variety of different materials. In some embodiments the body portion 20 is formed from a rigid material selected to maintain its curved shape during use. The rigid material may have a curvature selected to conform to the shape of a patients face to allow comfortable placement of the endotracheal tube holder 10.

The body portion 20 can also include additional components that allow comfortable attachment to a patient. For example, the body portion 20 can include two enlarged pad regions 55 at opposite ends. The enlarged pad regions 55 provide a widened surface area for placement against the patient's body, e.g., against the patient's cheeks or head. In addition the endotracheal tube holder can include regions for attachment to a band of flexible material. For example, in certain embodiments the endotracheal tube holder includes band openings 60 located at opposite ends. The band openings 60 can receive a band such as a flexible elastic band, tape or other material to secure the endotracheal tube holder to a patient. In addition, the pad regions can include an adhesive or tacky surface that prevents movement or sliding, and may also include cushioned or padded surfaces. Moreover, in certain embodiments, the body portion 20 can further attach to an elongated pad 51. On one surface, the elongated pad 51 can attach to the back of the body portion 20. On the other surface, the elongate pad 51 attaches to the a region of the patient's face, for example, between the upper lip and the nose of the patient. In certain embodiments, the elongated pad 51 can be made of a soft material to provide a cushion against the harder surface of the body portion 20 and to provide comfort to the patient. In certain embodiments, such as those shown in FIGS. 1-5 and 7, the pad 51 is almost as long as the elongated opening 50. Moreover, in certain embodiments, the pad 51 includes an opening which overlaps the elongated opening 50, such that the pad 41 does not block the elongated opening 50.

As discussed above, the endotracheal tube holder 10 can include a tube grasping mechanism 30. The tube grasping mechanism allows secure attachment of an endotracheal tube 65, thereby preventing unintended movement or dislodgement. The tube grasping mechanism 30 can include a variety of different configurations. For example, as shown in FIGS. 1-5, the tube grasping mechanism 30 can include a rigid plastic or other rigid material to allow secure attachment of an endotracheal tube 65. In some embodiments, the tube grasping mechanism 30 can include a upper semi-circular region 70 to receive an endotracheal tube. The tube grasping mechanism 30 can also include an lower semi-circular region 75 and a hinge or pivot region 80 to attach the lower semi-circular region 75 to the upper semi-circular region 70. The hinge or pivot region 80 provides a pivotable connection between the lower semi-circular region 75 and the upper semi-circular region 70. The pivotable connection 80 allows the tube grasping mechanism 30 to be opened and closed to secure the endotracheal tube 65 in place.

Figure 2:
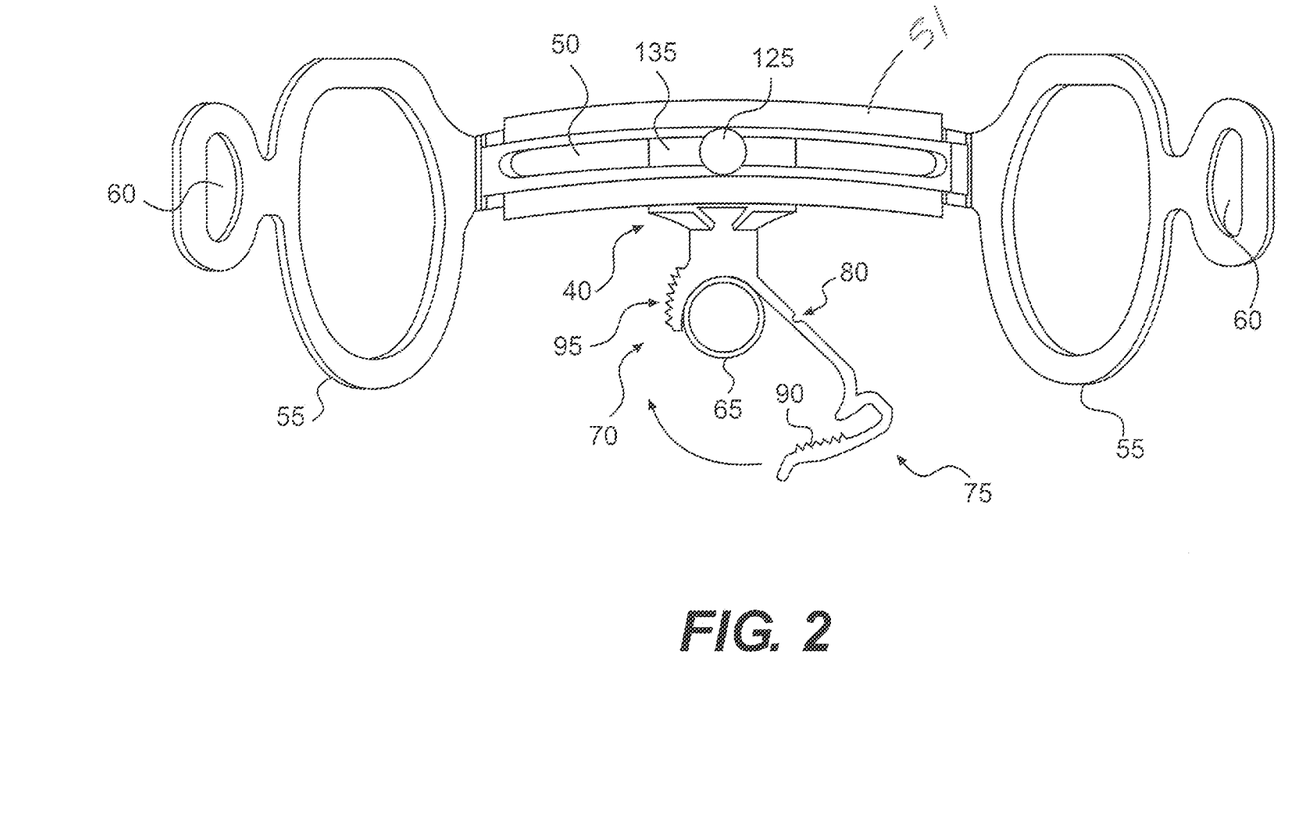
FIG. 2 provides a rear view of the endotracheal tube holder of FIG. 1.
Figure 3:
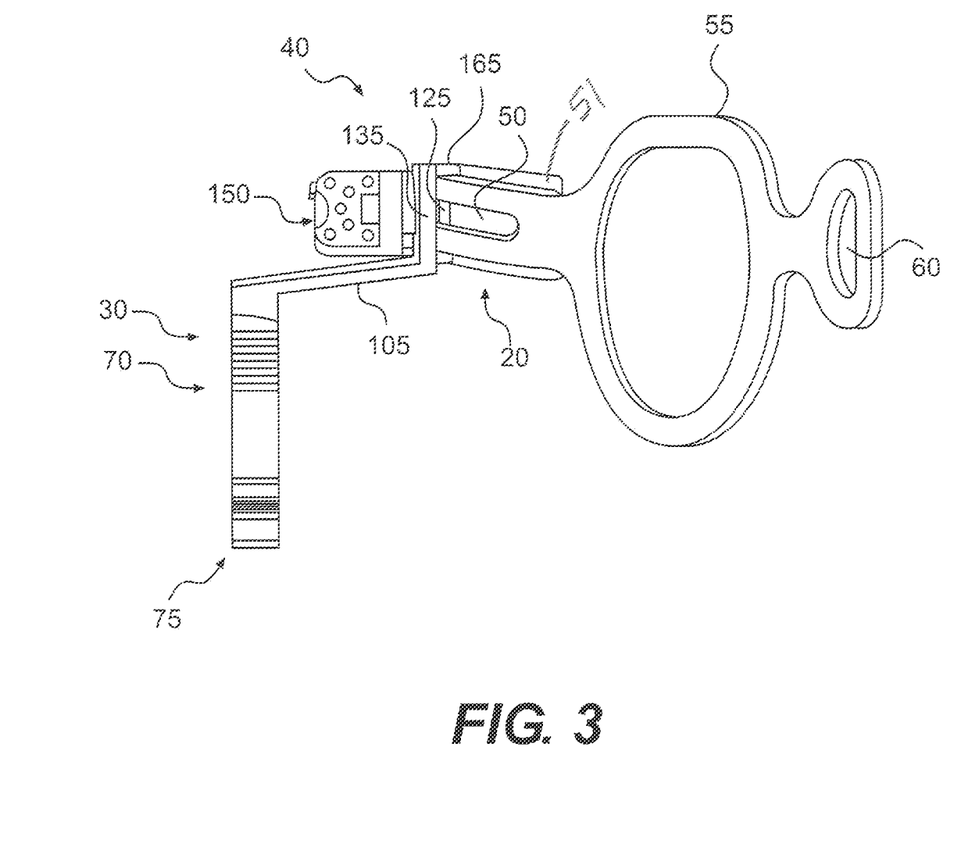
FIG. 3 provides a side view of the endotracheal tube holder of FIG. 1.
Figure 4:
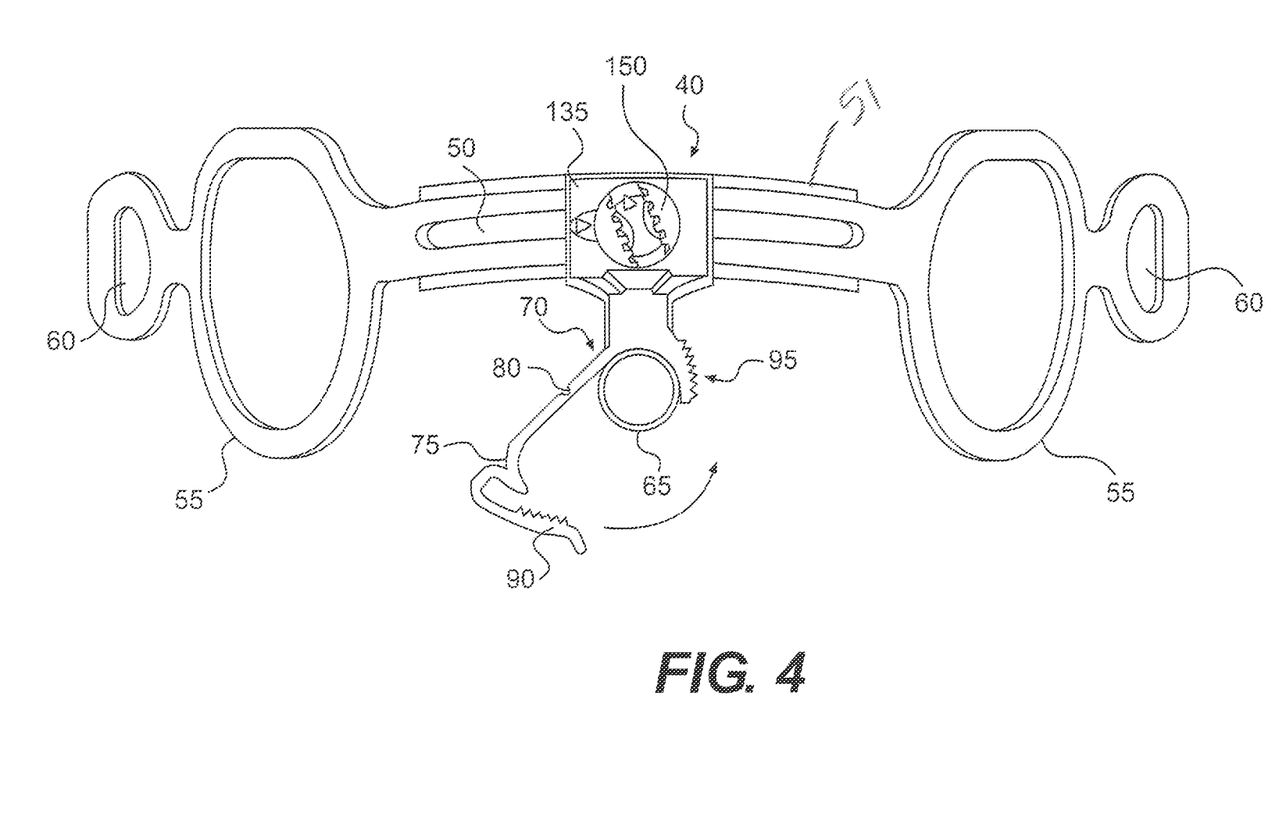
FIG. 4 provides a front view of the endotracheal tube holder of FIG. 1.
Figure 5:
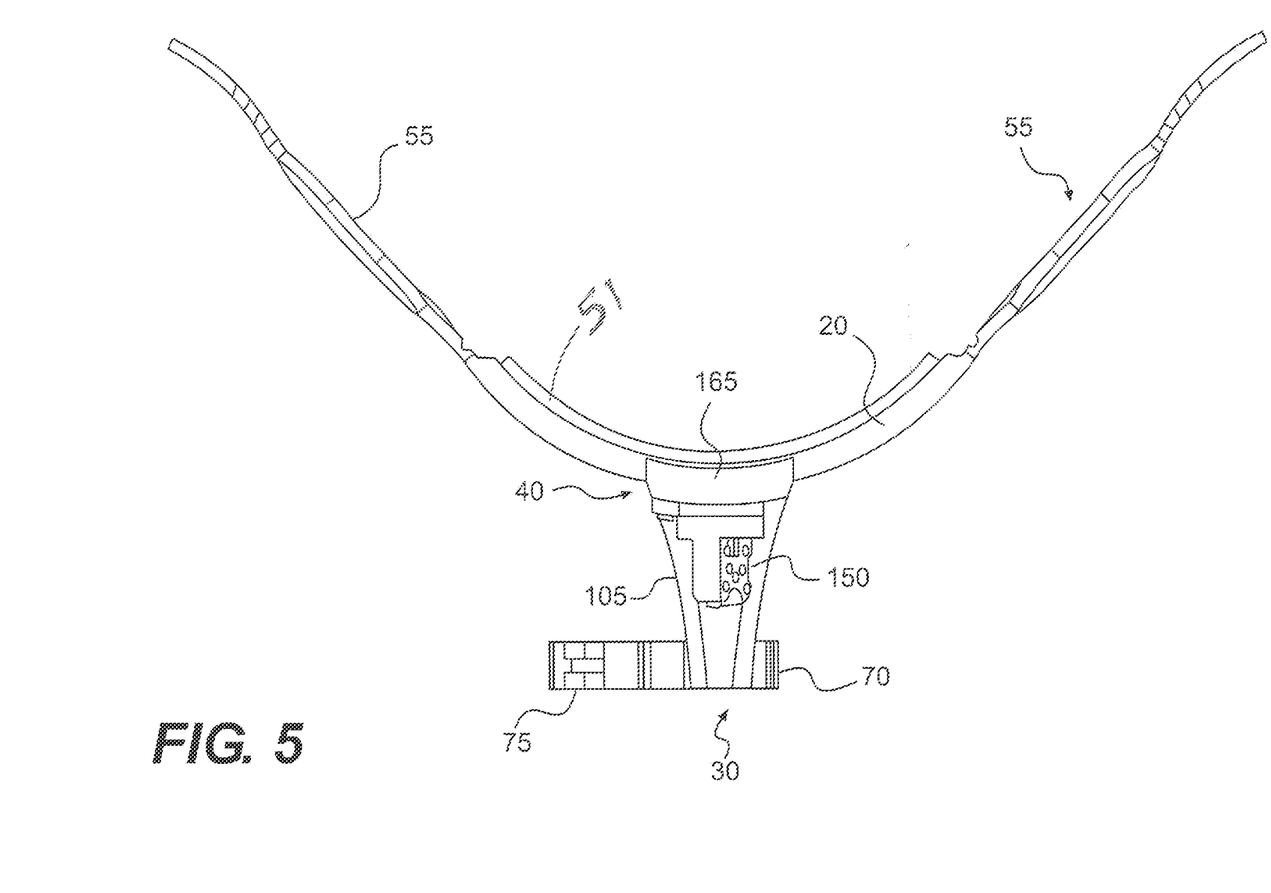
FIG. 5 provides a bottom view of the endotracheal tube holder of FIG. 1.

The tube grasping mechanism can also include systems to allow secure closure of the tube grasping mechanism. For example as shown in FIGS. 2 and 4, the tube grasping mechanism 30 can include teeth 90 and 95 on the upper and lower semi-circular regions 70 and 75, respectively. The teeth 90, 95 can engage one another to allow closure with a desired degree of pressure around the endotracheal tube.

As alternatives to the tube grasping mechanism depicted in FIGS. 1-5, other tube grasping mechanisms may be used in conjunction with the body portion 20 and attachment mechanism 40. For example, the tube grasping mechanism 30 can include non-rigid closures, such as a flexible band, including VELCRO®. Alternatively, the tube grasping mechanism can simply include a flat or curved platform to which tape or other connecting materials can be applied. For example, in one embodiment, the tube grasping mechanism 30 can include one of the upper semi-circular region 70 or the lower semi-circular region 75 to receive an endotracheal tube 65, and the tube can be held in place using tape, adhesives, a rigid cap, or other connectors.

The tube grasping mechanism 30 can be connected to the attachment mechanism 40 to allow adjustable connection to the body portion 20. In some cases, the tube grasping mechanism 30 is connected to the attachment mechanism via a rigid connector or arm 105. The rigid connector or arm 105 allows the tube grasping mechanism 30 to be firmly positioned once the attachment mechanism 40 is secured in place along the body portion 20, as described further below.

As discussed above, the attachment mechanism 40 can include a system for adjustably securing the grasping mechanism 30 to the body portion 20. As shown in FIGS. 2 and 4, the elongated opening 50 provides a track along which the attachment mechanism 40 can be moved to adjust the position of an endotracheal tube 65.

Figure 6:
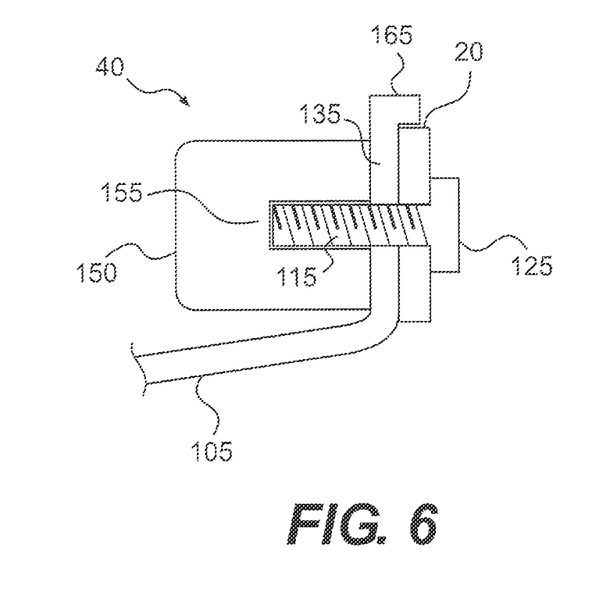
FIG. 6 provides a side cutaway view of an attachment mechanism of endotracheal tube holders, according to exemplary embodiments.

FIG. 6 provides a cutaway view of an attachment mechanism 40 for adjustably securing the tube grasping mechanism 30 to the body portion 20. As shown, the attachment mechanism 40 can include a rod portion 115 that passes through the elongated opening 50 of the body portion 20. Further, in certain embodiments, the tube grasping mechanism 30 includes a widened end surface 135 attached to the end of the arm 105, which is clamped to the body portion 20 by the attachment mechanism. The attachment mechanism 40 can include a widened rod end 125 and a locking cap 150, which are positioned on opposite sides of, and clamp together, the widened end surface 135 and the body portion 20. The rod portion 115, by passing through the elongated opening 50 and connecting to the widened rod end 125 to a locking cap 150, forms a clamping mechanism that can releasably secure the tube grasping mechanism 30 to the body portion 20. Further, in some cases, widened end surface 135 attaches to an upper lip 165 that serves to stabilize the attachment mechanism 40 against the body portion 20.

The rod portion 115, the widened rod end 125, and the widened end surface 135 can include a variety of configurations. In some cases, the rod portion 115 includes a rod or similar elongated structure. In addition, the rod portion 115 can include a threaded body that passes through the elongated opening 50. The threaded rod portion 115 can be connected to the widened rod end 125 and the widened end surface 135 in a variety of ways. For example, in some cases, the rod portion 115 forms a threadable (e.g., nut and bolt arrangement) connection with at least one of the widened rod end 125 and the widened end surface 135. In some cases, as shown in FIG. 6, the rod portion 115 passes through a portion of the widened end surface 135 on the side of the attachment mechanism 40 that connects to the tube grasping mechanism 30. The rod portion 115 can simply pass through an opening in the widened end surface 135 or can form a threaded connection with the opening and widened end surface 135.

In addition, as described above and shown in FIG. 6, the rod portion 115 can connect to the widened rod end 125 on the opposite side of the opening 50. The connection with the widened rod end 125 on the opposite side of the opening can be a threaded or removable connection, or can be a permanent connection. For example, the rod portion 115 and the widened rod end 125 can be formed from a single piece of material or can be joined, e.g. by sonic welding or using other suitable joining mechanisms such as adhesives, chemical bonding, or snap fit connections.

The attachment mechanism 40 can include a system to allow the widened rod end 125 and the locking cap 150 to clamp to the body portion 20 and the widened end surface of the tube grasping mechanism 30. For example, as shown, the dimensions of the widened rod end 125 and the locking cap 150, and also the dimensions of the widened end surface 135 and the upper lip 165, prevent them from passing through the elongated opening 50. In addition, force can be applied to the widened rod end 125 and the widened end surface 135 to allow the surfaces to clamp the body portion and hold the body portion 20 in place. For example, as shown in FIG. 6, the locking cap 150 can be a threaded locking cap. The locking cap 150 can include a threaded inner portion 155 that engages an end of the rod portion 115. Rotation of the locking cap 150 with respect to the rod portion 115, which can include a threaded outer surface, will change the distance between the widened rod end 125 and the widened end surface 135 to clamp or release the attachment mechanism 40 to the body portion 20. Moreover, in some embodiments, the widened rod end 125 and body portion 20 are selected such that friction between their surfaces prevents widened rod end 125 and the rod portion 115 from rotating when the locking cap 150 is rotated. Accordingly, the position of the attachment mechanism 40 along the elongated opening 50 of the curved body can be adjusted, and the attachment mechanism 40 can be tightened to clamp the attachment mechanism 40 and tube grasping mechanism 30 in place. In various embodiments, the widened rod end 125 and the widened end surface 135 and body portion 20 can be selected to produce sufficient friction to prevent movement of the tube grasping mechanism 30 when the attachment mechanism is locked or clamped in a selected position.

Figure 7:
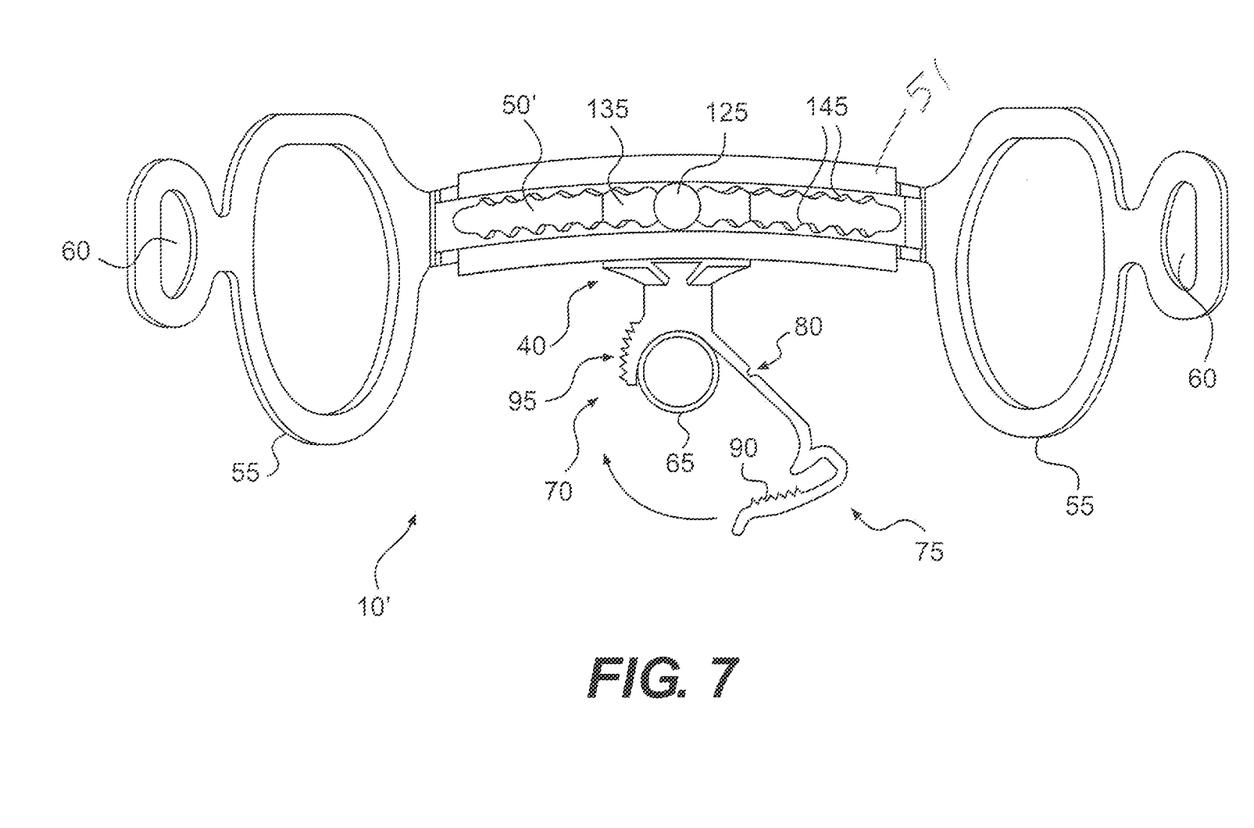
FIG. 7 provides a rear view of an endotracheal tube holder, according to certain embodiments of present disclosure.

FIG. 7 provides a rear view of an endotracheal tube holder, according to certain embodiments of present disclosure. The endotracheal tube holder 10' of FIG. 7 is similar to the tube holder 10 described above. However, in some cases, as pointed out in FIG. 7, the elongated opening 50' of the body portion 20 can include surface configurations to stabilize the attachment mechanism. For example, as shown, at least one edge of the elongated opening can include curves or teeth 145. The curves or teeth can conform to the shape of the rod portion 115 to receive the rod portion 115 and prevent sliding of the attachment mechanism 40. In various embodiments, the teeth or the curves can be of various sizes, which can depend on the size of the tube or the specific use.

Figure 8:
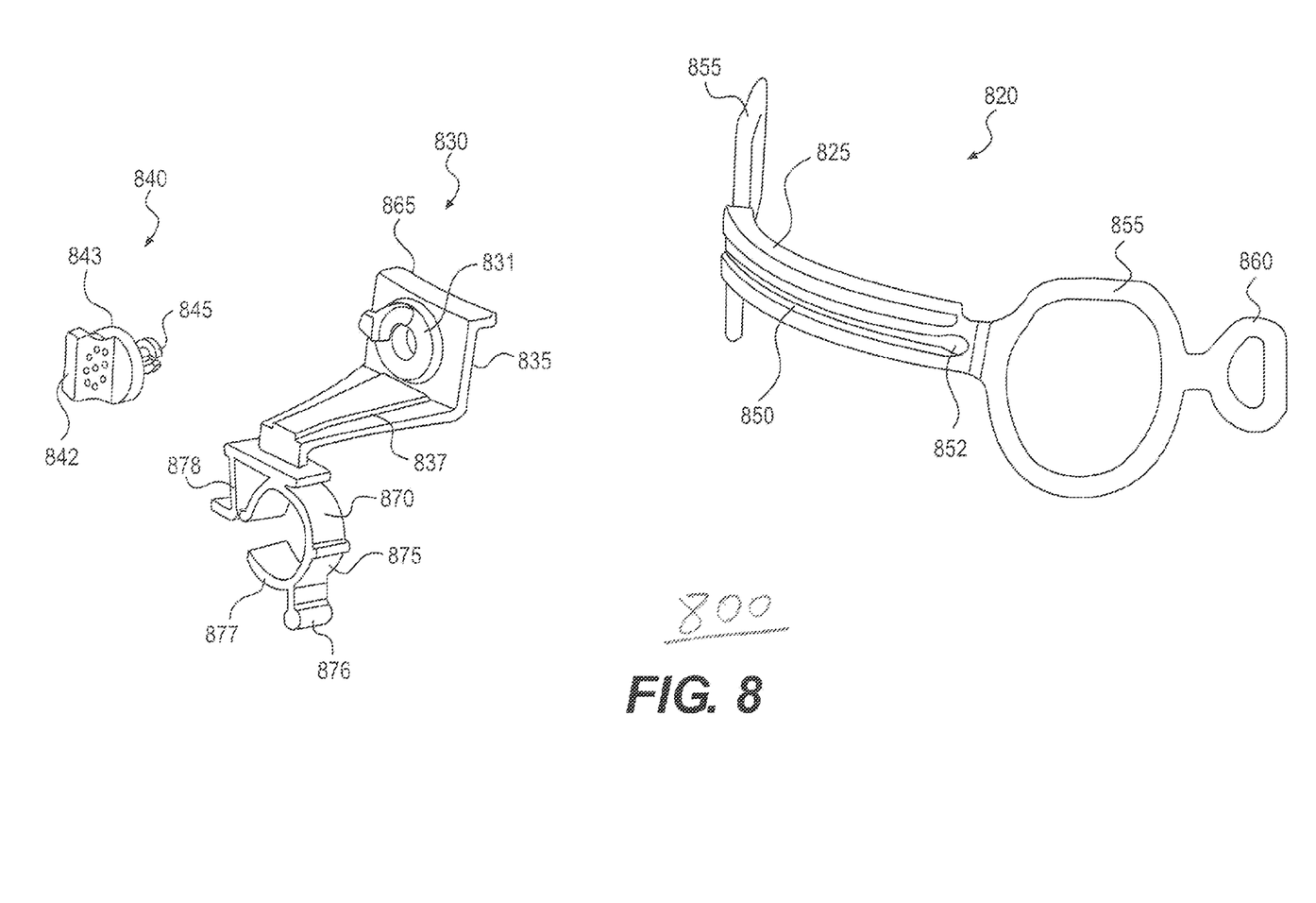
FIG. 8 shows an exploded view of an endotracheal tube holder according to certain embodiments of present disclosure.

FIG. 8 shows an exploded view of an endotracheal tube holder 800 according to certain embodiments. Endotracheal tube holder 800 can include at least three parts: a body portion 820, a tube grasping mechanism 830, and an attachment mechanism 840. When assembled, attachment mechanism 840 attaches tube grasping mechanism 830 to body portion 820. Unless stated otherwise, different sections of the endotracheal tube holder 800 are designed and function in a manner similar to the corresponding sections of other embodiments described in FIGS. 1-7.

Figure 9:
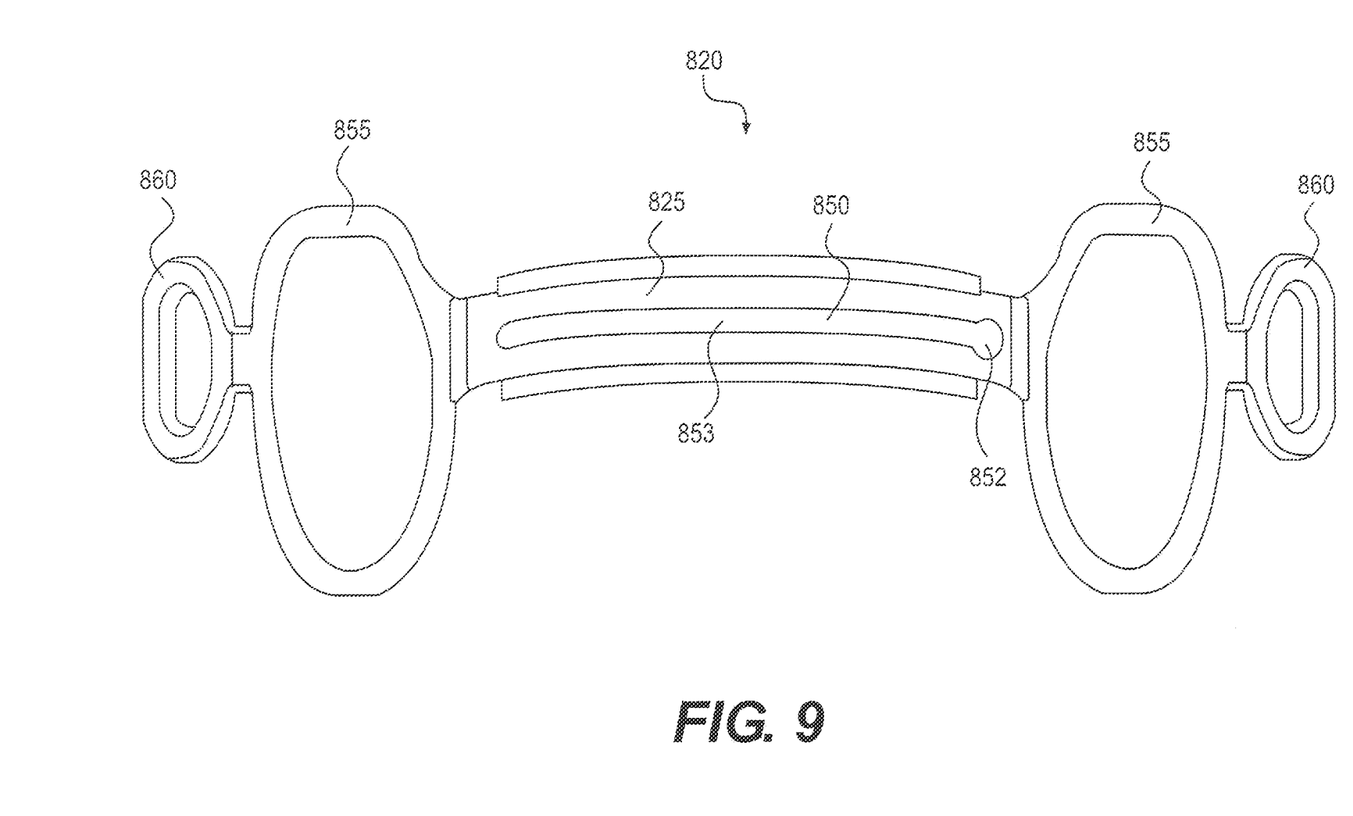
FIG. 9 shows a front view of a body portion of the endotracheal tube holder of FIG. 8.

FIG. 9 shows a front view of the body portion 820 of FIG. 8. The body portion 820 includes an elongated middle section 825, two enlarged pad regions 855 attached to the opposite ends of the middle section 825, and two band openings 860 attached to the two pad regions 855. Middle section 825 includes an elongated opening 850. In certain embodiments shown in FIGS. 8 and 9, the elongated opening 850 is in the form of an elongated slit for directing the attachment mechanism 840 to which the tube grasping mechanism 830 is attached. Also, in certain embodiments, the elongated opening 850 widens at one end, forming a wide opening 852. The remainder of the elongated opening 850, i.e., slit 853, is narrower that the wide opening 852. In FIGS. 8 and 9, wide opening 852 is in the form of a open circle. In various embodiments, the opening can have other shapes, such as open oval or rectangular. In some embodiments, wide opening 852 is sized for receiving the attachment mechanism 840, and the narrow slit 853 is configured for holding and leading that mechanism, as explained below in more detail.

Figure 10:
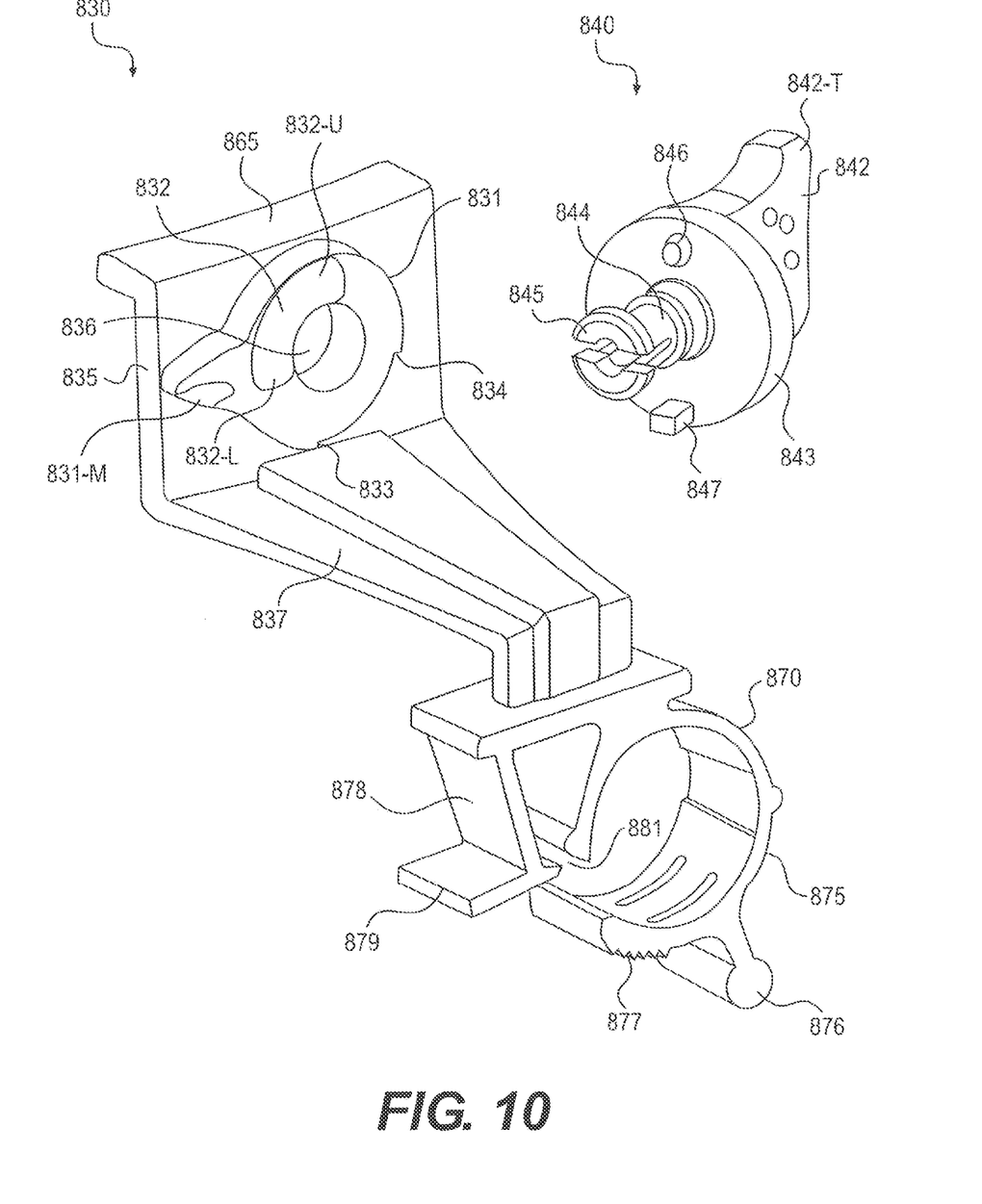
FIG. 10 shows detailed side views of a grasping mechanism and an attachment mechanism of the endotracheal tube holder of FIG. 8.

FIG. 10 shows detailed side views of the grasping mechanism 830 and the attachment mechanism 840 of FIG. 8. The tube grasping mechanism 830 includes an upper lip 865, a widened end surface 835, an arm 837, upper and lower semicircular regions 870 and 875, and locking lever 878.

In some embodiments, the upper and lower semicircular regions 870 and 875, and the locking lever 878 provide a tube-locking mechanism to receive and secure a tube. For example, in certain embodiments, the lower semicircular region 875 includes a lower handle 876 and end section 877. Moreover, the locking lever 878 includes a lever handle 879. In some embodiments, the region attaching the upper and lower semicircular regions 870 and 875 is made of a flexible material. When using the tube holder, to receive a tube, a user inserts the end section 877 through the gap 881 by, for example, pulling lever 878 away and opening the gap 881. The user thus creates a tube receiving area between the upper and lower semicircular regions 870 and 875. The user can then insert the tube into the tube receiving area. If the area is too narrow for receiving a selected tube, a user can widen the tube receiving area by moving the lower semicircular region 875 away from the upper semicircular region 870 using, for example, the lower handle 876. Similarly, to tighten the tube receiving area around the tube, a user can narrow the tube-receiving area by pushing the lower semicircular region 875 towards the upper semicircular region 870 using, for example, the lower handle 876 or by pushing the lower semicircular region 875 from below. As a result of these narrowing or widening actions, the end section 877 moves up or down through the gap 881.

In some embodiments, the locking lever 878 can lock the end section 877 and secure the tube in place. In the embodiment shown in FIG. 10, for example, the outer surface of end section 877 is toothed. Further, the locking lever 878 and the area attaching this lever to the arm 837 can be made of flexible materials with spring-like characteristics, such as a living hinge. The locking lever 878 and the left half of upper semicircular region 870 thus create a pincer that can lock the end section 877 in place. When the user releases the lever handle 879, the lever 878 moves back in, such that the end of lever 878 engages the teeth on the outer surface of end section 877 and locks the pincer on the end section 877. In various embodiments, the length of the toothed section the end section 877 varies, to enable the tube grasping mechanism 830 to secure tubes of various sizes.

Using the above mechanism, a user can insert and lock a tube in endotracheal tube holder 800. The user locks the tube by narrowing the tube receiving area to a size that is snug fit to the tube and then locking the end section 877 with the lever 878. In some embodiments, the inner surface of the upper semicircular region 870 or the lower semicircular region 875 includes a rough surface to create friction with the tube and thus prevent the tube from slipping through the tightened receiving area. In some embodiments, one or both the inner surfaces of the semicircular regions includes some grabbing teeth for creating the friction.

FIGS. 8 and 10 also show some details of the attachment mechanism 840, according to some embodiments. This attachment mechanism includes a knob handle 842, a knob cap 843, a middle rod 844, and a bulge 845. In some embodiments, the attachment mechanism 840 is a unitary piece, in which the parts, that is, the knob handle 842, the knob cap 843, the middle rod 844, and the bulge 845 are fixed to each other. In some embodiments, these parts are made as one piece using one mold.

When assembling the endotracheal tube holder 800, an assembler can use the attachment mechanism 840 to attach the tube grasping mechanism 830 to the body portion 820. In some embodiments, the diameter of bulge 845 is almost equal to or slightly less than the diameter of the wide opening 852 and is larger than the width of the narrow slit 853. The diameter of the middle rod 844, on the other hand, is almost equal or smaller than the width of the narrow slit. The diameter of the bulge 845 is also smaller than or almost equal to the dimension of the middle opening 836 in the center of the end surface 835. In these embodiments, the assembler needs little or no force to pass the bulge 845 first through the middle opening 836 and then through the wide opening 852.

Further, in certain embodiments, a disassembler can disassemble the endotracheal tube holder 800. To disassemble the endotracheal tube holder 800, in certain embodiments, the disassembler can remove the attachment mechanism 840 from the body portion and the grasping mechanism. To do that, the disassembler moves the attachment mechanism to the end of the narrow slit 853 where the wide opening 852 is located, such that bulge 845 is positioned behind wide opening 852. The disassembler then removes the attachment mechanism by respectively pulling out the bulge 845 through the wide opening 852 and the middle opening 836. In certain other embodiments, once assembled and in the normal course of use, the endotracheal tube holder 800 will not be disassembled.

In some embodiments, the bulge 845 is made of a flexible material, and its diameter is slightly larger than the width of the wide opening 852. Moreover, as shown in FIG. 10, in some embodiments the bulge 845 includes an open slit in the middle. In some embodiment, due to the open slit or its spring-like characteristics, the bulge also possesses a spring like characteristic along a diameter perpendicular to the slit, such that it collapses when pinched and returns to its original size when the pinching force is removed. In these embodiments, the assembler first passes bulge 845 through the middle opening 836 and then, to pass the bulge through wide opening 852, the assembler has to use some force. Due to its spring like characteristics, when pinched or pushed into the wide opening 852, bulge 845 shrinks, passes through the wide opening 852, and then opens up. In this manner, due to its size, bulge 845 locks behind the wide opening 852.

Further, in certain embodiments, a disassembler can disassemble the endotracheal tube holder 800. In certain embodiments, to disassemble the endotracheal tube holder 800, the disassembler first moves the attachment mechanism to the end of the narrow slit 853 where the wide opening 852 is located, such that bulge 845 is positioned behind wide opening 852. Further, to pull the bulge out of the wide opening 852, the disassembler can first press the bulge 845 to a smaller size before moving through wide opening 852. The disassembler then removes the attachment mechanism by pulling out the bulge 845 through the wide opening 852 and the middle opening 836. In certain other embodiments, once assembled and in the normal course of use, the endotracheal tube holder 800 will not be disassembled.

In some embodiments, the elongated opening 850 does not include a wide opening. In these embodiments, the assembler can press the bulge through the elongated opening or the disassembler may remove the bulge from the elongated opening by shrinking the bulge using the force of pressing or by a pinching force. In various embodiments, an assembler or a disassembler can be a technician or a machine in the manufacturing factory, a technician in the medical facility, or any other end user.

In some embodiments, when using the assembled endotracheal tube holder 800, the user moves the grasping mechanism 830 and the attachment mechanism 840 along the middle section 825. During these movements, the middle rod 844 moves through narrow slit 853. In these situations, bulge 845, which is larger than narrow slit 853, holds the attachment mechanism attached to the middle section 825. When the user moves the grasping mechanism 830 to a desired position, the user then secures the grasping mechanism in place by tightening the attachment mechanism 840 such that it clamps the middle section 825 of body portion 820 to the widened end surface 835 of the tube grasping mechanism 830.

In some embodiments, the user performs the tightening by turning knob handle 842 in one direction, and performs the untightening and thus unclamping by turning the knob handle 842 in the opposite direction. The tightening and untightening are achieved by a set of tightening features included in the widened end surface 835 of the tube grasping mechanism 830 and the knob cap 843 of the attachment mechanism 840.

In some embodiments, as shown in FIG. 10, the tightening features of the widened end surface 835 are included in the a protruded surface 831 located at the front surface of the widened end surface 835. These tightening features of the protruded surface 831 include a tightening groove 832 formed on its surface. The tightening features also include a cut out of the lower right side of the protruded surface 831, as shown in FIG. 10. This lower right cut out covers approximately one fourth of the perimeter of the protruded surface 831 and creates two stopper teeth at its two end points shown in FIG. 10; a lower stopper tooth 833 located approximately at the lowest point on the perimeter of the protruded surface 831, and a side stopper tooth 834 located approximately at the right-most point on that perimeter.

The tightening features of the knob cap 843 can be included on the rear surface of the knob cap 843. These features include a tension tang 846 and a positive stopper 847.

When the assembler assembles the three parts of the endotracheal tube holder 800, that is, the body portion 820, the tube grasping mechanism 830, and the attachment mechanism 840, the tightening features of inner surface of the knob cap 843 fit against the tightening features of the protruded surface 831. For example, in the embodiments shown in FIG. 10, the assembler lays the widened end surface 835 of the tube grasping mechanism against the middle section 825 of the body portion, such that the upper lip 865 lies over the upper edge of the middle section 825. Moreover the assembler lines up the middle opening 836 with the wide opening 852. The assembler then orients the attachment mechanism 840 such that knob handle 842 is in "open" position, that is the knob handle is approximately parallel to the outer edges of the end surface 835 as, for example, shown in FIG. 10. The assembler then attaches the attachment mechanisms to the end surface 835 and the middle section 825 that have been laid together, by passing the bulge 845 through the middle opening 836 and through the wide opening 852.

In the assembled configuration, the attachment mechanism 840 sandwiches together the body portion 820 and the grasping mechanism 830. In particular, a clamping mechanism is formed by three pieces, the bulge 845 as the rear end, the knob cap 843 as the front end, and the middle rod 844 connecting these two ends. The two clamping ends sandwich between them two sandwiched surfaces, that is, the middle section 825 of the body portion and the widened end surface 835 of the tube grasping mechanism. The length of the middle rod 844 is such that in the assembled configuration and when the knob is in the open position, the space between the two ends of the clamp is almost the same as the combined thickness of the sandwiched surfaces. Therefore, in this position, the protruded surface 831 attaches to the inner surface of the knob cap 843. The length of the middle rod 844 is also such that in the open position of the knob, the clamp ends do not press the sandwiched surfaces too tightly, allowing them to move freely against each other.

Upon such attachment, tightening features of the two surfaces fits against each other. For example, tension tang 846 fits in the upper portion of the groove 832 and stopper 847 fits inside the lower right cut out next to the lower stopper tooth 833. Because the pieces are not tightly clamped in this situation, a user can move the tube grasping mechanism 830 along the middle section 825 by moving the middle rod 844 inside the elongated opening 850. After moving the tube grasping mechanism to the desired position, the user can secure it in place by tightening the clamping mechanism. In the embodiment shown in FIG. 10, the user tightens the clamping mechanism by turning knob handle 842 approximately 90 degrees counter-clockwise from the open position to a "closed" position. In this embodiment, in the closed position the knob handle orients approximately perpendicular to the outer edges of the end surface 835 and the tip 842-t of the knob handle lies against a mark 831-M on the left side of the protruded surface 831.

During the tightening turn, the movement of the tightening features against each other determines the range of the turn and also creates the tension required for tightening the clamp. For example, the combination of the stopper and the stopper teeth creates a stopping mechanism that limits the range of tightening turn, and the combination of the tension tang and the groove creates a clamping tension. Regarding the stopping mechanism, when the user turns the knob handle counter-clockwise, the stopper 847 moves counter-clockwise inside the lower right cut out until it reaches the side stopper tooth 834. Side stopper tooth 834 thus stops the knob handle from turning further.

Regarding the clamping tension, the closing turn causes the sandwiched surfaces to push against the clamping surfaces. For example, on the rear end of the clamping mechanism, the bulge contacts the surface of the middle section. On the front side of the clamping mechanism, the knob cap 843 contacts the widened end surface, and more specifically, the tip of the tension tang 846 contacts the surface of the groove 832. The surface of the groove is made with a gradual taper in its depth. That is, the upper part 832-U of the groove is deeper than its lower part 832-L. When the knob turns counter clockwise from the open position to the closed position, the tension tang 846, which is in contact with the groove at the upper part 832-U, moves to the lower part 832-L of the groove. Due to the change of depth, with this movement the groove pushes the tension tang 846 forward. This forward push transfers through the middle rod 844 to the bulge 845, thus clamping the middle section 825 and the widened end surface 835. In effect, the tightening turn causes the effective total thickness of the sandwiched surfaces to increase, thus adding to the pressure between the sandwiched surfaces and the sandwiching surfaces of the clam.

In various embodiments, characteristics of the clamping mechanism and the clamped surfaces are such that the tightening turn locks the sandwiched surfaces to each other. In some embodiments, these characteristics include the amount of taper in the depth of the groove, the flexibility characteristics of the middle rod, and the friction coefficient between the two sandwiched surfaces, that is, the contacting surfaces of the body portion and the widened end surface. These characteristics are such that the tightening turn increases the contact friction between the two sandwiched surfaces by an amount that is sufficient for preventing the tube grasping mechanism 830 from moving with respect to the body portion 820.

In some embodiments, a user can release the tube grasping mechanism by turning the knob clockwise from the closed position to the open position. Such opening turn causes the tension tang 846 to move from the shallower lower part 832-L of the groove to the deeper upper part 832-U of the groove. This move decreases the effective total thickness of the sandwiched surfaces, thus reducing the tension in the middle rod 844. Accordingly, this untightening turn reduces the contact friction between the two sandwiched surfaces, allowing the tube grasping mechanism 830 to move with respect to the body portion 820.

Figure 11:
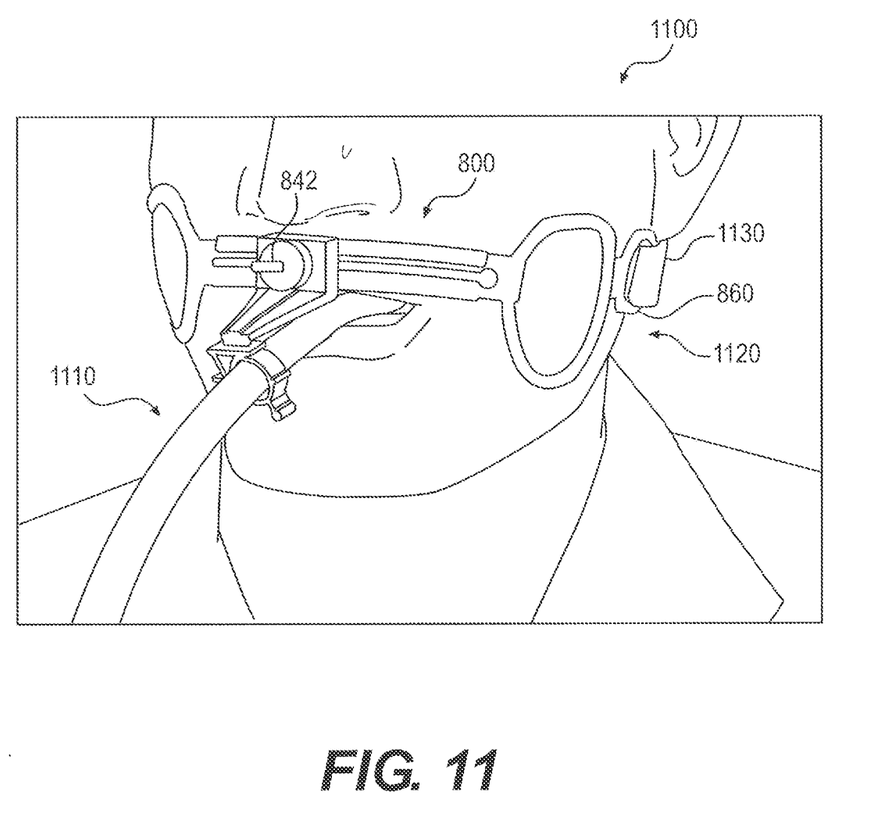
FIG. 11 shows a view of an assembled endotracheal tube holder holding a tube against the face of a patient, according to certain embodiments of present disclosure.

FIG. 11 shows a view 1100 of an assembled endotracheal tube holder 800 holding a tube 1110 against the face of a patient 1120, according to an embodiment. In the view 1100, a user has secured endotracheal tube holder 800 to the face of the patient 1120 by threading a band 1130 through band openings 860 and securing the band behind the head of the patient. In some embodiments, the band 1130 includes two complement mechanical attachment materials on its two surfaces. The user, after tightening the band 1130 around the patient's neck or head, can tie the band's end securely by fitting the two mechanical attachment mechanisms against each other. In some embodiments, the complement mechanical attachment materials include VELCRO® loop and hook materials. Further, in the embodiment shown in FIG. 11, a user has positioned the tube 1110 slightly to the left of the middle of the patient's mouth and has secured the tube in place by turning the knob handle to the closed position. In certain embodiments, tube holder 800 also includes two adhesive pads. Each of the adhesive pads attaches to one of the pad regions on one surface and to the face of the patient on the other surface. In various embodiments, the adhesive pads can be of different shapes, e.g., circular, oval, or rectangular. In some embodiments, adhesive pads are sized such that each fully covers the corresponding pad region.

It will be apparent to those skilled in the art that additional various modifications and variations can be made consistent with the present disclosure. Other embodiments consistent with the tube holder will be apparent to those skilled in the art from consideration of the specification and practice of the disclosure. It is intended that the specification and examples be considered as exemplary only, with a true scope and spirit of the disclosure being indicated by the following claims.

The invention claimed is:

1. An endotracheal tube holder comprising:
    a tube grasping mechanism; and
    a body portion, wherein the body portion is elongated and comprises an elongated opening in the form of an elongated slit along a horizontal axis of the body portion, the elongated slit permitting lateral adjustment and securing of an attachment mechanism to any location along the elongated slit, for adjustably securing the tube grasping mechanism to the body portion,
    the attachment mechanism adjustably securing the tube grasping mechanism to the body portion, the attachment mechanism comprising:
        a rod member configured to pass through the elongated opening;
        a widened proximal body connected to a proximal end of the rod member; and
        a widened distal body attached to a distal end of the rod member, having a size that prevents the widened distal body from passing through the elongated opening to secure the attachment mechanism to the body portion, and the widened distal body having a smooth, vertical surface parallel to and pressed against smooth, vertical surfaces on the body portion immediately below and above the elongated opening, whereby the pressing is predominantly accomplished through at least one force orthogonal to these surfaces.

2. An endotracheal tube holder comprising:
    a tube grasping mechanism; and
    a body portion, wherein the body portion is elongated and comprises an elongated opening in the form of an elongated slit along a horizontal axis of the body portion, the elongated slit permitting lateral adjustment and securing of an attachment mechanism to any location along the elongated slit, for adjustably securing the tube grasping mechanism to the body portion,
    the attachment mechanism adjustably securing the tube grasping mechanism to the body portion, the attachment mechanism comprising:
        a rod member configured to pass through the elongated opening;
        a widened proximal body connected to a proximal end of the rod member; and
        a widened distal body attached to a distal end of the rod member, having a size that prevents the widened distal body from passing through the elongated opening to secure the attachment mechanism to the body portion, and wherein at least one end of the elongated slit includes a widened opening for receiving the widened distal body.

3. The tube holder of claim 2, wherein the widened distal body has a spring like property along at least one dimension configured to being forcibly pushed through the widened opening and for locking behind the body portion.

4. The tube holder of claim 2, wherein the widened distal body has a spring like property along at least one dimension configured to being forcibly pushed through a section of the elongated opening and for locking behind the body portion.

5. The tube holder of claim 1, wherein the rod member comprises a threaded rod.

6. The tube holder of claim 5, wherein at least one of the widened proximal body and the widened distal body includes a threaded locking cap such that rotation of the locking cap with respect to the threaded rod changes a distance between the widened proximal body and the widened distal body to clamp or release the attachment mechanism to or from the body portion.

7. The tube holder of claim 6, wherein the tube grasping mechanism comprises a widened end surface in which a middle opening is formed for receiving the rod member, wherein the rod member is rigidly connected to the widened distal body at the distal end, and wherein the widened proximal body includes the locking cap, such that the threaded rod passes through the elongated opening and the middle opening and is threadably connected to the locking cap.

8. The tube holder of claim 2, wherein the tube grasping mechanism comprises a widened end surface in which a middle opening is formed for receiving the rod member, wherein the widened end surface is for attaching to the body portion, and wherein the widened proximal body and the widened distal body sandwich between them the body portion and the widened end surface.

9. The tube holder of claim 2, wherein the body portion is curved for conforming to the shape of the face of a patient.

10. The tube holder of claim 1, wherein the tube grasping mechanism comprises an upper semicircular region and a lower semicircular region pivotably attached to the upper semicircular region.

11. The tube holder of claim 10, wherein the upper semicircular region and the lower semicircular region comprise teeth to lock the lower semicircular region to the upper semicircular region and secure a tube therebetween.

12. The tube holder of claim 10, wherein the lower semicircular region includes a tail end and the upper semicircular region includes a pincer configured to receive and lock the tail end and accordingly secure a tube between the upper and the lower semicircular regions.

13. The tube holder of claim 12 wherein the tail end is toothed on at least one surface.

14. The tube holder of claim 2, wherein the body portion further comprises widened pad regions at opposite ends for lying against the face of a patient.

15. The tube holder of claim 14, further comprising a band opening on each of the widened pad regions for receiving a flexible band for tying around the head or the neck of the patient.

16. The tube holder of claim 1, wherein the body portion comprises a rigid material.

17. The tube holder of claim 2, further comprising an arm that connects the tube grasping mechanism to the attachment mechanism.

18. The tube holder of claim 1, wherein the elongated opening includes a toothed surface on at least one side.

19. An endotracheal tube holder, comprising:
a tube grasping mechanism; and
a body portion, wherein the body portion is elongated and comprises an elongated opening in the form of an elongated slit along a horizontal axis of the body portion, the elongated slit permitting lateral adjustment and securing of an attachment mechanism to any location along the elongated slit, for adjustably securing the tube grasping mechanism to the body portion,
the tube grasping mechanism rigidly connected to the attachment mechanism adjustably securing the tube grasping mechanism to the body portion, the attachment mechanism comprising:
a rod member that passes through the elongated opening;
a widened proximal body connected to a proximal end of the rod member; and
a widened distal body attached to a distal end of the rod member, having a size that prevents the widened distal body from passing through the elongated opening to secure the attachment mechanism to the body portion, and the widened distal body having a smooth, vertical surface parallel to and pressed against smooth, vertical surfaces on the body portion immediately below and above the elongated opening, whereby the pressing is predominantly accomplished through at least one force orthogonal to these surfaces.

20. The tube holder of claim 19, wherein the tube grasping mechanism comprises an upper semicircular region and a lower semicircular region pivotably attached to the upper semicircular region, and wherein the upper semicircular region and the lower semicircular region comprise teeth to lock the lower semicircular region to the upper semicircular region and secure a tube therebetween.

21. The tube holder of claim 19, wherein the rod member comprises a threaded body and wherein at least one end of the threaded body is connected to a threaded locking cap such that rotation of the locking cap with respect to the rod member changes a distance between widened surfaces on opposite sides of the elongated opening to clamp or release the attachment mechanism.

22. The tube holder of claim 21, wherein the rod member is rigidly connected to one of the widened surfaces on one side of the elongated opening.

23. An endotracheal tube holder, comprising:
a tube grasping mechanism; and
a body portion, wherein the body portion is elongated and comprises an elongated opening in the form of an elongated slit along a horizontal axis of the body portion, the elongated slit permitting lateral adjustment and securing of an attachment mechanism to any location along the elongated slit, for adjustably securing the tube grasping mechanism to the body portion,
the attachment mechanism adjustably securing the tube grasping mechanism to the body portion, the attachment mechanism comprising:
a rod member configured to pass through the elongated opening;
a widened distal body attached to a distal end of the rod member, wherein at least one end of the elongated slit of the elongated slit includes a widened opening for receiving the widened distal body.

24. An endotracheal tube holder, comprising:
a tube grasping mechanism; and
a body portion, wherein the body portion is elongated and comprises an elongated opening in the form of an elongated slit along a horizontal axis of the body portion, the elongated slit permitting lateral adjustment and securing of an attachment mechanism to any location along the elongated slit, for adjustably securing the tube grasping mechanism to the body portion,
the tube grasping mechanism rigidly connected to the attachment mechanism adjustably securing the tube grasping mechanism to the body portion, the attachment mechanism comprising:
a rod member that passes through the elongated opening;
a widened proximal body connected to a proximal end of the rod member; and
a widened distal body attached to a distal end of the rod member, having a size that prevents the widened distal body from passing through the elongated opening to secure the attachment mechanism to the body portion, and wherein at least one end of the elongated slit includes a widened opening for receiving the widened distal body.

* * * * *